United States Patent [19]

Manzo

[11] Patent Number: 4,763,670
[45] Date of Patent: Aug. 16, 1988

[54] MICROBIOLOGICAL SPECIMEN SAMPLING DEVICE

[75] Inventor: Michael P. Manzo, Upton, Mass.

[73] Assignee: Microvasive, Inc., Milford, Mass.

[21] Appl. No.: 909,850

[22] Filed: Sep. 19, 1986

[51] Int. Cl.⁴ .............................................. A61B 10/00
[52] U.S. Cl. ..................................... 128/756; 128/759
[58] Field of Search .................... 128/749, 751–754, 128/756, 759; 604/36, 165, 54–55

[56] References Cited

U.S. PATENT DOCUMENTS

| | | | |
|---|---|---|---|
| 2,739,585 | 3/1956 | Ayre | 128/756 |
| 2,767,703 | 10/1956 | Nieburgs | 128/749 |
| 3,037,495 | 6/1962 | Naz | 128/759 |
| 3,777,743 | 12/1973 | Binard et al. | 128/749 |
| 3,800,781 | 4/1974 | Zalucki | 128/749 |
| 3,857,384 | 12/1974 | Watson | 128/749 |
| 4,136,680 | 1/1979 | Southworth | 128/759 |
| 4,227,537 | 10/1980 | Suciu et al. | 128/756 |
| 4,235,244 | 11/1980 | Abele et al. | 128/749 |
| 4,318,414 | 3/1982 | Schuster et al. | 128/759 |
| 4,324,262 | 4/1982 | Hall | 128/756 |
| 4,457,313 | 6/1984 | Alter | 128/759 |
| 4,485,824 | 12/1984 | Koll | 128/756 |
| 4,532,935 | 8/1985 | Wang | 128/753 |
| 4,534,362 | 8/1985 | Schumacher et al. | 128/738 |
| 4,586,604 | 5/1986 | Alter | 128/756 X |

FOREIGN PATENT DOCUMENTS

| | | | |
|---|---|---|---|
| 0031228 | 7/1981 | European Pat. Off. | 128/756 |
| 2735706 | 2/1978 | Fed. Rep. of Germany | 128/749 |

OTHER PUBLICATIONS

Medi Tech; Contamination Free Microbiology Specimen Brush 10/1978.

Primary Examiner—Kyle L. Howell
Assistant Examiner—Angela D. Sykes

[57] ABSTRACT

A microbiological specimen sampling device capable of operation by one hand to both expose the sample collector and obtain contamination-free specimens consists of a catheter assembly including: an outer catheter and an inner catheter, each having distal and proximal ends, a sample collector disposed generally within the inner catheter and having operating structure for extending the sample collector beyond the distal ends of the catheters to obtain a sample, and a removable, water soluble plug engaging and sealing a portion of the outer catheter in a position between the distal ends of the outer and inner catheters. The device also includes structure for moving the outer catheter axially with respect to the inner catheter consisting of a first handle member at the proximal end of the outer catheter, and a second handle member at the proximal end of the inner catheter and located proximally of the first handle member, the handle members defining respective surfaces adapted and arranged for operating engagement by different digits of one hand of an operator to be drawn together to cause relative axial movement of the inner and outer catheters to dislodge the plug from the outer catheter by pushing-out motion of the inner catheter, and the device includes structure for operation of the sampling device by a digit of the same hand while grasping the proximal end of the catheter assembly.

5 Claims, 2 Drawing Sheets

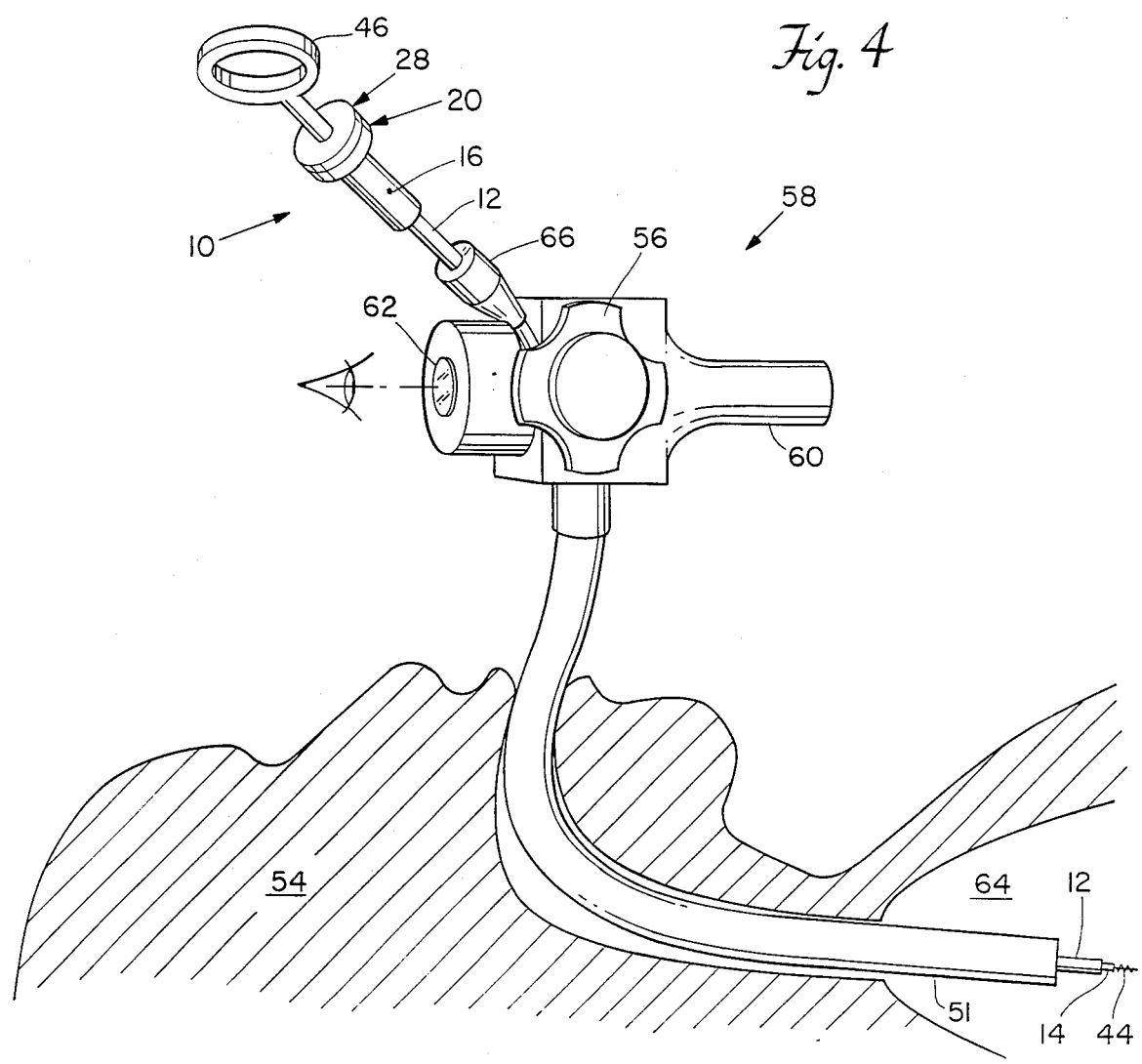
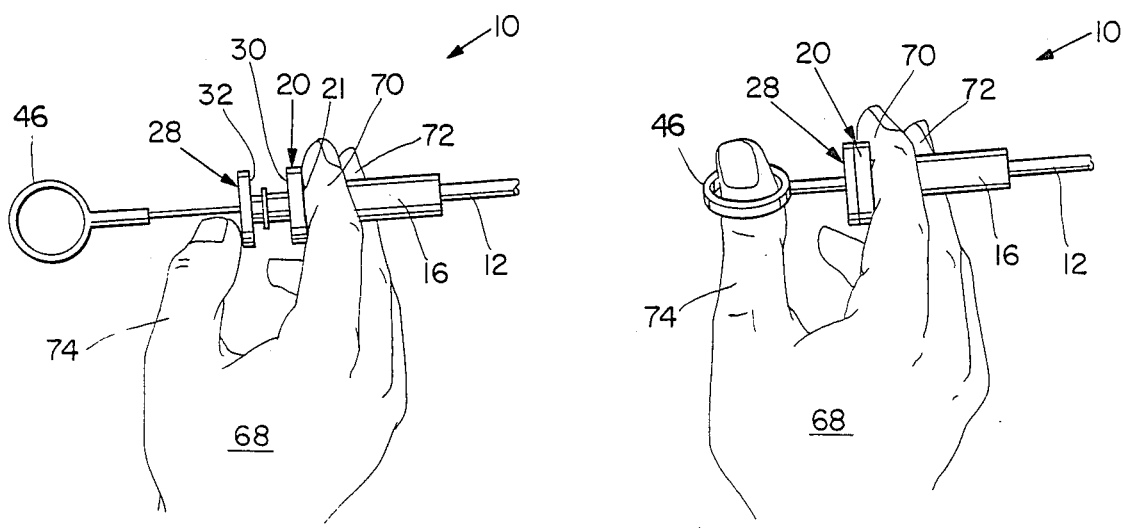

MICROBIOLOGICAL SPECIMEN SAMPLING DEVICE

The invention relates to microbiological specimen sampling devices of the type capable of use through the working channel of an endoscope to obtain a specimen within the body.

The sampling device typically consists of a specimen brush disposed within a tubular sheath during introduction and removal from the body. After the physician guides the device through the endoscope inside the body, to a position where it is desired to take a specimen, and while continuing to control the endoscope to view the site, the physician operates the handle of the sampling brush, which extends outside the body, to project the brush distally out of the sheath and work it back and forth within the body to collect the specimen.

Abele et al., in U.S. Pat. No. 4,235,244, for the purpose of keeping the sampling brush sterile until use at the sampling site, taught the use of inner and outer sheaths about the brush, the distal end of the outer sheath initially closed by a plug of water soluble material, e.g., wax, that is discharged within the body at the time it is desired to collect the sample. The plug was ejected at the site by movement of the inner sheath, containing the sampling brush, distally relative to the outer sheath. As embodied in the Microbiology Specimen Brush, manufactured for Microvasive, Inc., of Milford, Mass., ejection of the wax plug required a two-handed operation by the physician.

SUMMARY OF THE INVENTION

According to the invention, a microbiological specimen sampling device capable of operation by one hand to both expose the sample collector and obtain contamination-free specimens, comprising a catheter assembly comprises: an outer catheter having a distal end and a proximal end, and an inner catheter having a distal end and a proximal end, a sample collector disposed generally within the inner catheter and having operating means for extending the sample collector beyond the distal ends of the catheters to obtain a sample, a removable, water soluble plug engaging and sealing a portion of the outer catheter in a position between the distal end of the outer catheter and the distal end of the inner catheter, means for moving the outer catheter axially with respect to the inner catheter comprising: a first handle member at the proximal end of the outer catheter, and a second handle member at the proximal end of the inner catheter and located proximally of the first handle member, the handle members defining respective surfaces adapted and arranged for operating engagement by different digits of one hand of an operator to be drawn together to cause relative axial movement of the inner and outer catheters to dislodge the plug from the outer catheter by pushing-out motion of the inner catheter, and the operating means of the sampling device adapted to be operated by a digit of the same hand while the hand grasps the proximal end of the catheter assembly.

In preferred embodiments, the handle members further include means for limiting longitudinal separation of the respective handle member surfaces to a predetermined maximum distance; the first handle member comprises a longitudinally extending handle sleeve and the second handle member comprises a longitudinally extending handle shaft, the handle shaft being sized and constructed to telescope into the handle sleeve upon urging of the respective handle member surfaces together, preferably the handle members further include stop means for retaining the handle shaft within the handle sleeve; and the device further comprises means for fixing the relative positions of the catheters during obtaining of a sample.

The objectives of the present invention include providing a microbiological specimen sampling device that is operable by the physician to eject the wax plug and collect specimens within the body using one hand only, leaving the other hand free.

These and other objectives and features of the invention will be understood from the following description of a preferred embodiment, and from the claims.

PREFERRED EMBODIMENT

We first briefly describe the drawings.

DRAWINGS

FIG. 4 is a somewhat diagrammatic view of the sampling device of the invention in use through a flexible boroscope, while FIGS. 4a and 4b are similar views of the device during operation by a physician for ejection of the wax plug and for collection of a specimen, respectively.

The microbiological specimen sampling device 10 of the invention includes an outer catheter 12 and, disposed therewithin, an inner catheter 14, both of Teflon ® (polytetrafluroethylene) or other conventional catheter material. The outer catheter is of length sufficient to extend from outside the body to the position within the body where it is desired to obtain a sample, e.g., about 100 cm, and is of outer diameter selected to allow the device to be introduced into the body via the working channel of a flexible endoscope, e.g., the typical working channel has a diameter of about 1.8 mm, and the outer catheter OD is about 0.070 inch. The inner catheter is about the same length, and has an outer diameter, e.g., about 0.053 inch, selected to allow the inner catheter to be moved axially within the outer catheter.

Figure 1:
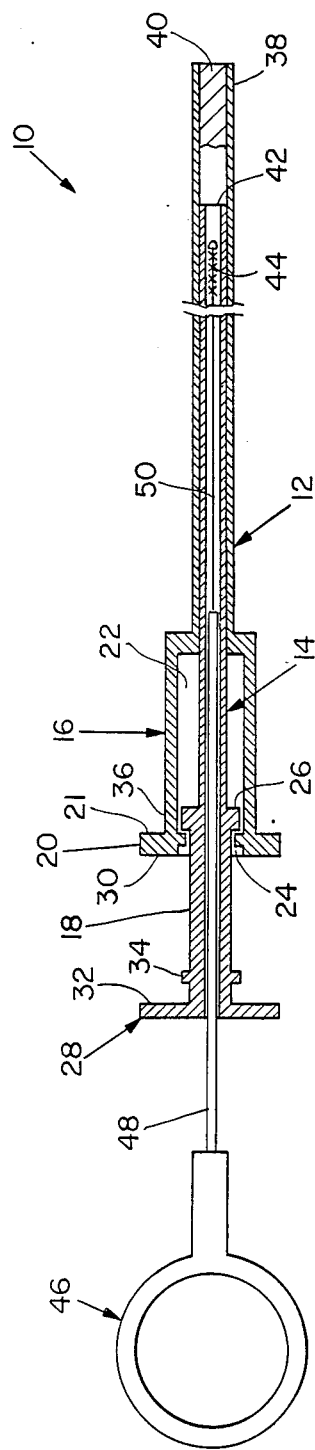
FIG. 1 is a side section view of the microbiological sampling device of the invention as introduced into the patient with the wax plug in place.
Figure 2:
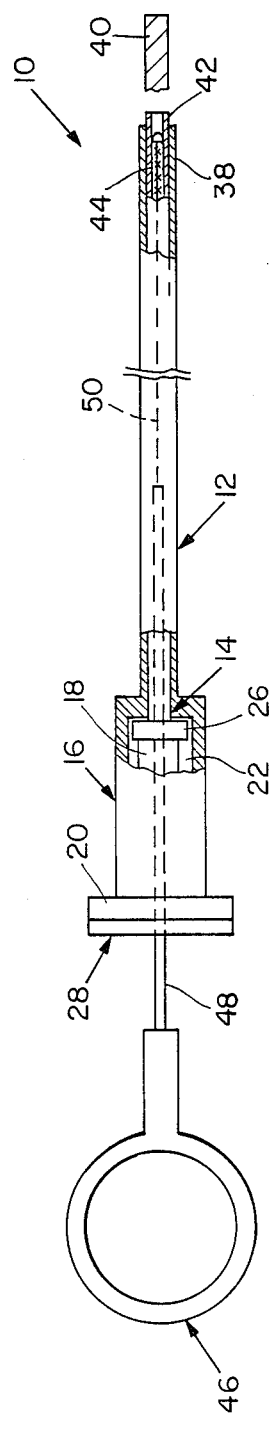
FIG. 2 is a similar view of the device with the wax plug ejected.
Figure 3:
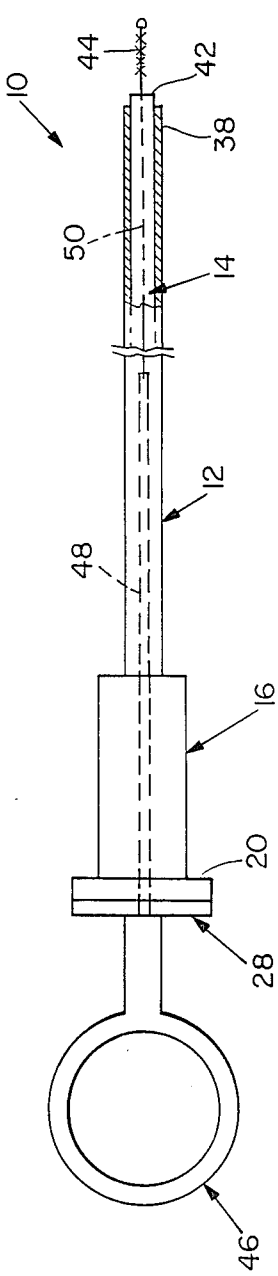
FIG. 3 is a side plan view of the device with the brush extended distally for sampling.

The outer and inner catheters terminate proximally in first and second handle members 16, 18, respectively, both formed of plastic, e.g., modified acrylic, injected molded about the ends of the respective catheters. The first handle member 16 has the form of an elongated sleeve and terminates proximally in a flange 20 defining a radially outwardly extending distal surface 21 about the sleeve. Within member 16 there is defined a center bore 22, restricted in diameter at the proximal end by a radially inwardly extending retaining ring 24. The second handle member 18, connected to the proximal end of inner catheter 14, has the form of an elongated shaft, sized generally to telescope into the center bore of the first handle member, terminating distally in a radial flange 26, and terminating proximally in a radially outwardly extending flange 28. Flange 26 is of diameter sized relative to the inner diameter of the opening in ring 24 to cause the surface of the flange to engage upon the surface of the ring, providing a stop engagement for retaining the shaft within the sleeve when the shaft is drawing proximally relative to the sleeve (FIG. 1). Flange 28 of the second handle member and flange 21 of the first handle member define opposed stop surfaces 30, 32 that engage as the handle shaft telescopes into the handle sleeve to limit axial movement of the inner catheter relative to the outer catheter and position the distal ends of the catheters in the desired relationship (FIG. 2). Defined about the handle shaft, distal of the engaging surface, is an annular rib 34 sized to slide through the center bore of the retaining ring and engage in a snap fit within an annular detent 36 defined by the wall of handle sleeve 16, to hold the handle sleeve and shaft together when the flange surfaces are engaged.

The distal end 38 of the outer catheter 12, as provided to the physician (FIG. 1), is sealed by a plug 40, e.g., about 2 mm in length, of material biologically compatible with the human body, e.g., a water soluble wax or wax-like plug, as described in U.S. Pat. No. 4,235,455, the disclosure of which is incorporated herein by reference. Disposed within the distal ehd 42 of the inner catheter 14 is a brush 44 for collecting samples of biological material. The sampling brush is connected, through the inner catheter, to a proximal thumbring 46, also of plastic, by a metal hypodermic tubing 48 and by wire 50, the tubing extending proximally from the thumbring, through the handle members and into the proximal end of the inner catheter to provide a stiffener against kinking of the wire during relative movement of the handle sleeve 16, handle shaft 18 and thumbring 46 during obtaining of samples, as we will now describe.

Referring to FIG. 1, the microbiological sampling device 10 of the invention is provided to the physician in the relationship shown, with the distal end 38 of the outer catheter closed by plug 40. The handle shaft member 18 is disposed in its proximal-most position relative to the handle sleeve member 16, with the surfaces of flange 26 and ring 24 engaged. In this position, the distal end 42 of the inner catheter 14 lies proximal of the plug 40, with the brush 44 disposed therewithin, the stiffener tubing 48 extending about an inch from the proximal end of handle shaft member 18. In this condition, the brush and distal portion of the inner catheter are sterile.

The physician now introduces the distal viewing end portion 51 of a flexible endoscope 58 into the body 54 of a patient. Holding the endoscope by handle 60 and viewing through eyepiece 62, the physician, using the steering means 56 provided at the endoscope handpiece, steers the end of the scope to a position, e.g., in the lung 64, where he wishes to obtain a sample. Using his free hand, the physician introduces the distal end 38 of the microbiological sampling device 10, still closed by plug 40, through the endoscope valve 66 and feeds it through the working channel of the scope until the distal end of the device emerges from the distal end of the scope.

Referring now to FIG. 4a, the physician, using his one free hand 68, grasps the handle sleeve member 16 between two fingers 70, 72, with the fingers resting against distal surface 21 of flange 20. Using the thumb 74 of the same hand, the physician urges the opposed surfaces 30, 32 of the handle sleeve and shaft members toward each other, the shaft telescoping into bore 22, and at the same time advances the distal end of the inner catheter distally relative to the distal end of the outer catheter, the end of the inner catheter engaging against and dislodging plug 40. The physician continues to urge opposed surfaces 30, 32 together until they are engaged, with annular rib 34 about the shaft engaged in snap-fit within annular detent 36 in the wall of the center bore of handle sleeve member 16. In this condition, the distal end of the inner catheter, with the brush 44 still disposed therewithin, extends by a short length beyond the end of the outer catheter, and engagement of rib 34 within detent 36 holds the handle members and the inner and outer catheters in this position, with the sterile brush spaced from the non-sterile outer catheter to avoid contamination (FIG. 2).

Referring now to FIG. 4b, the physician, still using his free hand, moves his thumb 74 from flange 28 to thumbring 46, and, while observing through eyepiece 62, moves the thumbring back and forth to extend the brush 44 distally from within the inner catheter into the body to obtain a sample. During this procedure, the physician continues to grasp the handle sleeve member, into which the handle shaft member is fully telescoped, between his fingers 70, 72 to stabilize the device.

When a sample has been obtained, the sampling brush is withdrawn into the inner catheter, and removed from the body to be evaluated by standard procedures.

What is claimed is:

1. A microbiological specimen sampling device capable of operation by one hand for exposure of a sample collector and for obtaining contamination-free specimens, comprising
    a catheter assembly comprising:
    an outer catheter having a distal end and a proximal end, and an inner catheter having a distal end and a proximal end,
    a sample collector disposed generally within said inner catheter,
    a removable, water soluble plug engaging and sealing a portion of said outer catheter in a position between the distal end of said outer catheter and the distal end of said inner catheter, and
    means operable by one hand for moving said outer catheter axially with respect to said inner catheter and for extending said sample collector beyond the distal ends of said catheters to obtain a sample, comprising:
    a first handle member at the proximal end of said outer catheter,
    a second handle member at the proximal end of said inner catheter and located proximally of said first handle member, and
    operating means for said sample collector,
        said handle members defining respective surfaces adapted and arranged for operating engagement by different digits of one hand of an operator to be drawn together to cause relative axial movement of said inner and outer catheters to dislodge said plug from said outer catheter by pushing-out motion of said inner catheter, and
        said operating means of said sample collector adapted to be operated by a digit of the same hand while the hand grasps the proximal end of said catheter assembly.

2. The microbiological specimen sampling device of claim 1 wherein said handle members further include means for limiting longitudinal separation of the respective handle member surfaces to a predetermined maximum distance.

3. The microbiological specimen sampling device of claim 1 or 2 wherein said first handle member comprises a longitudinally extending handle sleeve and said second handle member comprises a longitudinally extending handle shaft, said handle shaft being sized and constructed to telescope into said handle sleeve upon urging of the respective handle member surfaces together.

4. The microbiological specimen sampling device of claim 3 wherein said handle members further include stop means for retaining said handle shaft within said handle sleeve.

5. The microbiological specimen sampling device of claim 1 wherein said device further comprises means for fixing the relative positions of the catheters during obtaining of a sample.

* * * * *